US012605183B2

(12) United States Patent
Jamous et al.

(10) Patent No.: US 12,605,183 B2
(45) Date of Patent: Apr. 21, 2026

(54) TISSUE REMOVING CATHETER WITH TISSUE-REMOVING ELEMENT HAVING OBLIQUE DISTAL END FACE

(71) Applicant: Medtronic Vascular, Inc., Santa Rosa, CA (US)

(72) Inventors: Aram Jamous, Athenry (IE); Alan Ryan, Galway (IE); Aran Murray, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 721 days.

(21) Appl. No.: 17/711,522

(22) Filed: Apr. 1, 2022

(65) Prior Publication Data

US 2022/0323098 A1     Oct. 13, 2022

Related U.S. Application Data

(60) Provisional application No. 63/173,597, filed on Apr. 12, 2021.

(51) Int. Cl.
*A61B 17/3207* (2006.01)
*A61B 17/32* (2006.01)

(52) U.S. Cl.
CPC ................. *A61B 17/320758* (2013.01); *A61B 2017/320004* (2013.01)

(58) Field of Classification Search
CPC ........ A61B 17/3207; A61B 17/320758; A61B 2017/22038; A61B 2017/320004; A61B 2090/08021
USPC ....................................................... 606/159
See application file for complete search history.

(56) References Cited

U.S. PATENT DOCUMENTS

| | | | |
|---|---|---|---|
| 6,596,006 B1 | 7/2003 | Kanz et al. | |
| 6,800,083 B2 * | 10/2004 | Hiblar ............ | A61B 17/320758 |
| | | | 606/171 |
| 9,468,457 B2 | 10/2016 | Blackledge et al. | |
| 10,646,248 B2 * | 5/2020 | Chanduszko .. | A61B 17/320725 |
| 2007/0088230 A1 * | 4/2007 | Terashi ................. | A61M 25/09 |
| | | | 600/585 |

(Continued)

FOREIGN PATENT DOCUMENTS

| | | |
|---|---|---|
| EP | 2941209 A1 | 11/2015 |
| EP | 3679878 A1 | 7/2020 |
| WO | 2010087910 A1 | 8/2010 |

OTHER PUBLICATIONS

Written Opinion for corresponding PCT Application No. PCT/IB2022/053424, Apr. 12, 2022, 8 pages, Rijswijk, Netherlands.

*Primary Examiner* — Jocelin C Tanner
(74) *Attorney, Agent, or Firm* — Stinson LLP

(57) ABSTRACT

A tissue-removing catheter for removing tissue in a body lumen includes an elongate catheter body. A tissue-removing element is operatively coupled to a distal end portion of the elongate catheter body. The tissue-removing element has a central axis. The tissue-removing element is configured to be rotated about its central axis to remove tissue from the body lumen. A distal end portion of the tissue-removing element includes a distal end face at a distal-most end of the tissue-removing element. The distal end face has a perimeter and a diameter extending through the central axis. Diametrically opposite points on the perimeter lie in a plane that is oblique to the central axis of the tissue-removing element.

16 Claims, 7 Drawing Sheets

(56)            References Cited

U.S. PATENT DOCUMENTS

| | | | | |
|---|---|---|---|---|
| 2008/0249553 | A1* | 10/2008 | Gruber .................. | A61M 1/842 |
| | | | | 606/171 |
| 2012/0109171 | A1* | 5/2012 | Zeroni ........... | A61B 17/320758 |
| | | | | 606/159 |
| 2014/0081306 | A1* | 3/2014 | Bowe ....................... | A61N 1/05 |
| | | | | 606/190 |
| 2018/0317952 | A1* | 11/2018 | Jamous ............. | A61M 25/0082 |
| 2020/0078038 | A1 | 3/2020 | Fleming et al. | |

* cited by examiner

20

20

TISSUE REMOVING CATHETER WITH TISSUE-REMOVING ELEMENT HAVING OBLIQUE DISTAL END FACE

CROSS-REFERENCE TO RELATED APPLICATIONS

This application claims the benefit of U.S. Application Ser. No. 63/173,597, filed Apr. 12, 2022.

FIELD

The present disclosure generally relates to a tissue-removing catheter, and more particularly, to tissue-removing catheter including a rotatable tissue-removing element having an oblique distal end face.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters may employ a rotating element which is used to abrade or otherwise debulk the unwanted tissue.

SUMMARY

In one aspect, a tissue-removing catheter for removing tissue in a body lumen comprises an elongate catheter body having a longitudinal axis and proximal and distal end portions spaced apart from one another along the longitudinal axis. The elongate catheter body is sized and shaped to be received in the body lumen. A tissue-removing element is operatively coupled to the distal end portion of the elongate catheter body. The tissue-removing element has a central axis and proximal and a distal end portions spaced apart from one another along the central axis of the tissue-removing element. The tissue-removing element is configured to be rotated about its central axis to remove tissue from the body lumen. The distal end portion of the tissue-removing element includes a distal end face at a distal-most end of the tissue-removing element. The distal end face has a perimeter and a diameter extending through the central axis. Diametrically opposite points on the perimeter lie in a plane that is oblique to the central axis of the tissue-removing element.

In another aspect, a tissue-removing catheter for removing tissue in a body lumen comprises an elongate catheter body having a longitudinal axis and proximal and distal end portions spaced apart from one another along the longitudinal axis. The elongate catheter body is sized and shaped to be received in the body lumen. A tissue-removing element is operatively coupled to the distal end portion of the elongate catheter body. The tissue-removing element has a central axis and proximal and a distal end portions spaced apart from one another along the central axis of the tissue-removing element. The tissue-removing element is configured to be rotated to remove tissue from the body lumen. The distal end portion of the tissue-removing element includes a distal end face at a distal-most end of the tissue-removing element. The distal end face has a perimeter extending around the opening and a diameter extending through the axis of the distal opening. Diametrically opposite points on the perimeter lie in a plane that is oblique to the central axis of the tissue-removing element. A distal opening extends through the distal end face. The distal opening in the distal end face has an axis.

A method of debulking a lesion in a blood vessel using a rotational atherectomy catheter comprises advancing a tissue-removing element of the rotational atherectomy catheter toward the lesion in the blood vessel. The tissue-removing element has a central axis and proximal and a distal end portions spaced apart from one another along the central axis of the tissue-removing element. The distal end portion of the tissue-removing element includes a distal end face at a distal-most end of the tissue-removing element. The distal end face has a perimeter and a diameter extending through the central axis. Diametrically opposite points on the perimeter lie in a plane that is oblique to the central axis of the tissue-removing element. The tissue-removing element is rotated about its central axis simultaneously with said advancing rotational atherectomy catheter through the blood vessel, whereby rotation of the oblique distal end face of the tissue-removing element is configured to facilitate release of the tissue-removing element if the distal end face engages an obstruction in the blood vessel as the rotational atherectomy catheter is advanced in the blood vessel.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
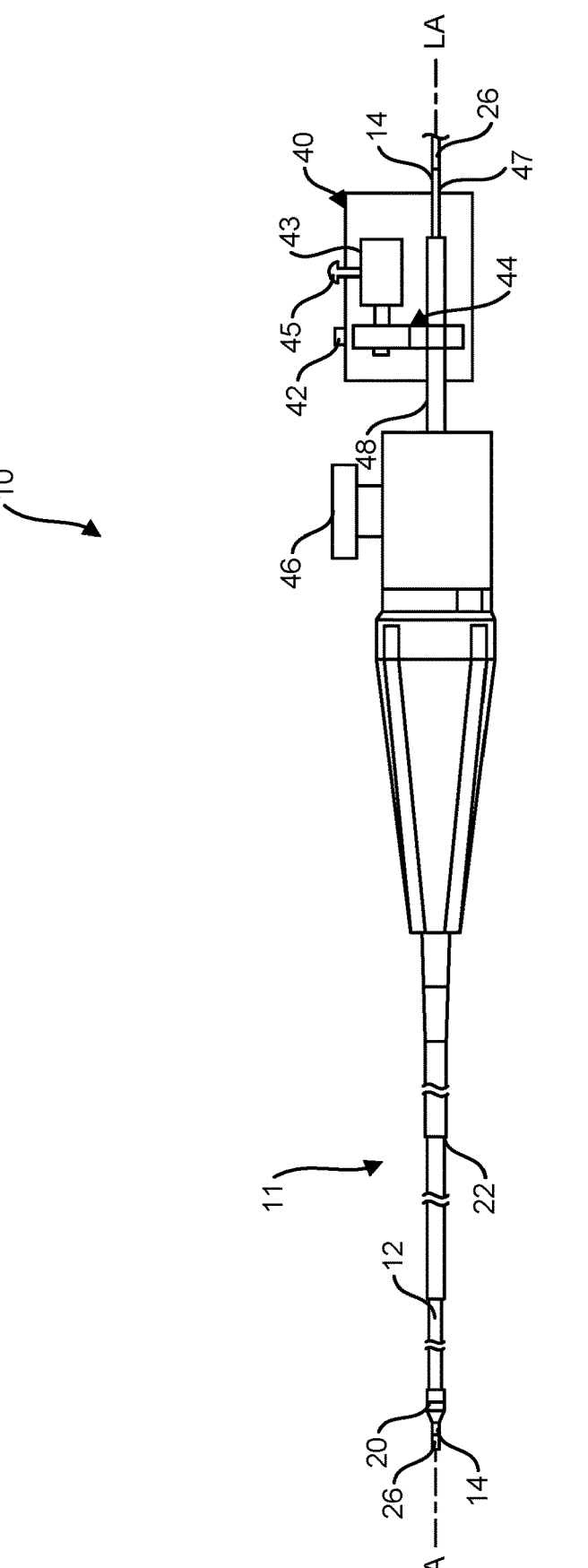
FIG. 1 is an elevation of a tissue-removing catheter of the present invention.

Referring to FIG. 1, a rotational tissue-removing catheter for removing tissue in a body lumen is generally indicated at reference number 10. The illustrated catheter 10 is a rotational atherectomy device suitable for debulking (e.g. abrading, cutting, excising, ablating, etc.) occlusive tissue (e.g. embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty PTCA or the subsequent delivery of a stent. Features of the disclosed embodiments may also be suitable for treating chronic total occlusion (CTO) of blood vessels, and stenoses of other body lumens, such as a ureter, a biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The illustrated catheter 10 is sized for being received in a blood vessel of a subject. While the remaining discussion is directed toward a catheter for removing tissue in blood vessels, it will be appreciated that the teaching of the present disclosure also applies to other types of tissue-removing catheters, including, but not limited to, catheters for penetrating and/or removing tissue from a variety of occlusive stenotic, or hyperplastic material in a variety of body lumens.

Figure 2:
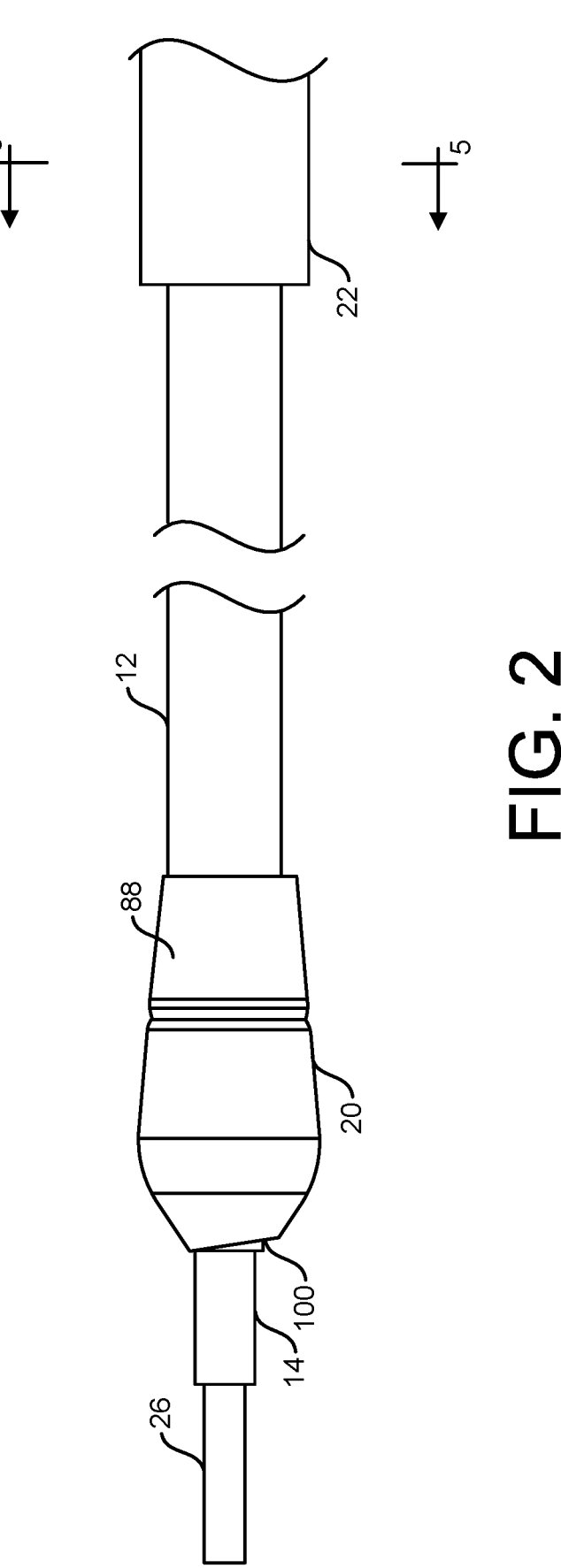
FIG. 2 is an enlarged elevation of a distal end portion of the catheter.

Referring to FIGS. 1 and 2, the catheter 10 comprises a catheter body, generally indicated at 11. The catheter body 11 includes an elongate drive shaft 12 and an elongate inner liner 14 received in an extending along the drive shaft. The drive shaft 12 and inner liner 14 extend along a longitudinal axis LA of the catheter body from a proximal end portion to a distal end portion of the catheter body. A tissue-removing element 20 is operatively coupled to a distal end of the drive shaft 12 and is configured for rotation to remove tissue from a body lumen, as will be explained in greater detail below. The drive shaft 12 may include a coiled elongate body, which may be formed from stainless steel or other material. A sheath 22 is disposed around the drive shaft 12. The drive shaft 12 and the inner liner 14 are both configured to translate (i.e., move longitudinally) relative to the sheath 22. The catheter body 11 and the sheath 22 are sized and shaped for insertion into a body lumen of a subject. The sheath 22 isolates the body lumen from at least a portion of the catheter body 11, and more particularly, at least a portion of the drive shaft 12.

The inner liner 14 defines a guidewire lumen 24 (FIG. 3) for slidably receiving a guidewire 26 therein so that the catheter body 11 can be advanced through the body lumen by traveling along the guidewire. The guidewire 26 can be a standard 0.014 inch (0.356 mm) outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). The guidewire lumen 24 extends from the proximal end portion through the distal end portion of the catheter body 11 such that the guidewire 26 is extendable along an entire working length of the catheter body. In one embodiment, the overall working length of the catheter 10 may be between about 135 cm (53 inches) and about 142 cm (56 inches). The inner liner 14 protects the guidewire 26 from being damaged from rotation of the drive shaft 12 by isolating the guidewire from the rotating drive shaft. The illustrated inner liner 14 also extends distally through the tissue-removing element 20 so that the distal end of the inner liner is exposed outside the tissue-removing element to protect the guidewire 26 from the rotating tissue-removing element.

Referring to FIG. 1, the catheter 10 further comprises a handle 40 secured at the proximal end portion of the catheter body. The handle 40 supports an actuator 42 (e.g., a lever, a button, a dial, a switch, or other device) configured to selectively actuate a drive, for example a motor 43, disposed in the handle to drive rotation of the drive shaft 12, and the tissue-removing element 20. In the illustrated embodiment, the motor 43 is coupled to the drive shaft 12 by a gear assembly 44 and an output shaft 48 supported by the handle 40. A slide or advancer 45 is positioned on the handle 40 and operatively coupled to the drive 43 to enable selective longitudinal advancement and retraction of the drive 43, the drive shaft 12, and tissue-removing element 20 relative to the handle 40 and the sheath 22. The handle 40 defines a slot which limits the movement of the slide 45 relative to the handle. Thus, the length of the slot determines the amount of relative movement between the drive shaft 12 and the handle 40. A perfusion port 46 may be disposed at the proximal end of the catheter 10. The port 46 communicates with a space between the sheath 22 and the drive shaft 12 for delivering fluid (e.g., saline) to cool the rotating drive shaft 12 during use. A proximal port 47 allows for passage of the guidewire 26 and inner liner 14 through the proximal end of the handle 40. A guidewire lock (not shown) may be provided on the handle 40 to lock the guidewire 26 in place relative to the handle, which may be desired during rotation of the tissue-removing element 20 to remove unwanted tissue in the body lumen.

Figure 3:
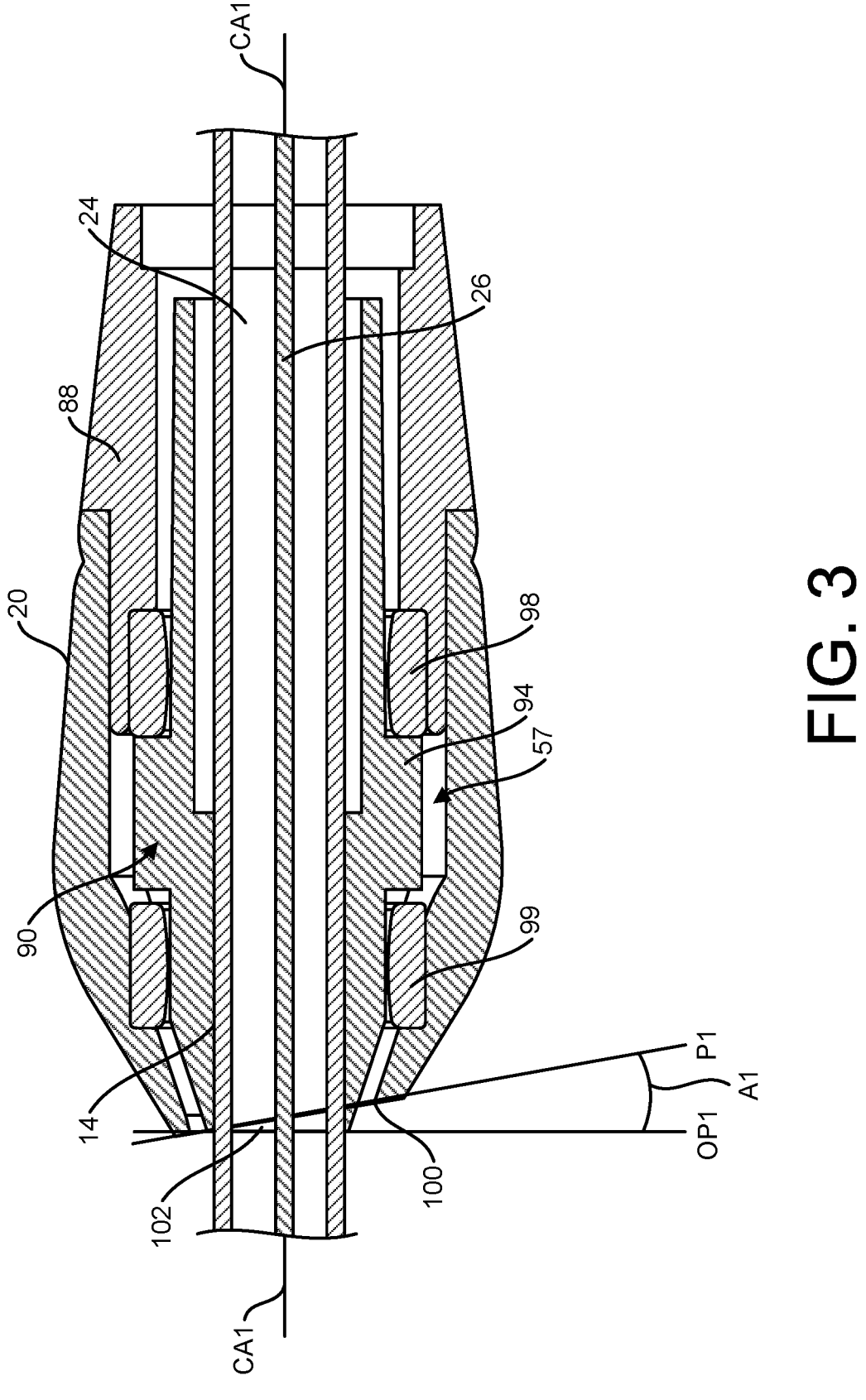
FIG. 3 is an enlarged fragmentary longitudinal cross section of the distal end portion of the catheter in FIG. 2.

In the illustrated embodiment, as shown in FIGS. 2 and 3, a drive shaft adaptor 88 couples the tissue-removing element 20 to the drive shaft 12 to transmit rotation from the drive shaft to the tissue-removing element. The drive shaft adaptor 88 is fixedly secured (e.g., welded) to a proximal end portion of the tissue-removing element 20 and fixedly secured (e.g., welded) to a distal end portion of the drive shaft 12. It is understood that the drive shaft 12 may be directly coupled to the tissue-removing element 20.

Referring to FIG. 3, the catheter 10 includes a coupling assembly, generally indicated at 57, coupling the tissue-removing element 20 to the inner liner 14. The illustrated coupling assembly 57 includes a bushing 90 and bearing rings (e.g., first and second bearing rings 98, 99) received around the bushing 90. An interior surface of the bushing 90 is fixedly attached to the inner liner 14. In one embodiment an adhesive such as an epoxy glue bonds the bushing 90 to the inner liner 14. As such, the bushing 90 does not rotate around the inner liner 14. The first and second bearing rings 98, 99 are coupled to the tissue-removing element 20 and/or the drive shaft adaptor 88. The bearing rings 98, 99 ride on the bushing 90 as the tissue-removing element 20 rotates. The first and second bearing rings 98, 99 are configured to engage a shoulder 94 of the bushing 90 so that translational movement of the drive shaft 12 is transmitted to the bushing 90 and the inner liner 14. The coupling assembly 57 isolates the tissue-removing element 20 from the inner liner 14 and is configured to enable rotation of the tissue-removing element about the inner liner. It is understood that the coupling assembly 57 may be omitted so that the tissue-removing element rotates directly on a guidewire or an inner liner.

Referring still to FIG. 3, the tissue-removing element 20 has a central axis CA1 and proximal and distal end portions spaced apart from one another along the central axis. As described above, the tissue-removing element 20 is operatively coupled to the distal end portion of the catheter body, and more specifically the drive shaft 12 in the illustrated embodiment. Rotation of the drive shaft 12 by the drive 43 imparts rotation of the tissue-removing element 20 about the central axis CA1 to remove tissue from the body lumen. In the illustrated embodiment, the central axis CA1 is aligned with the longitudinal axis LA of the catheter body 11. Also in the illustrated embodiment, the central axis CA1 is coextensive with longitudinal axes of the inner liner 14 and/or the bushing 90 and/or the guidewire 26 (when the guidewire is received in the inner liner). The illustrated tissue-removing element 20 comprises an abrasive outer surface configured to abrade tissue in the body lumen when the motor 43 rotates the abrasive burr. Thus, the illustrated tissue-removing element 20 may be considered an abrasive burr. The abrasive outer surface is formed, for example, by a diamond grit coating, surface etching, or the like. In other embodiments, the tissue-removing element 20 can compromise one or more cutting elements having smooth or serrated cutting edges, a macerator, a thrombectomy wire, etc. The tissue-removing element may be of other configurations and designs for suitably removing tissue in the body lumen as it is rotated.

As shown in FIG. 3, the distal end portion of the tissue-removing element 20 includes a distal end face 100 at a distal-most end of the tissue-removing element. The illustrated distal end portion of the tissue-removing element 20 is generally cone-shaped (e.g., truncated cone-shaped) having an outer diameter that tapers distally to the distal end face 100. The distal end face has a perimeter and a diameter extending through the central axis CA1. At least some diametrically opposite points on the perimeter lie in a plane P1 that is oblique to the central axis CA1 of the tissue-removing element 20. In this and other embodiments, all diametrically opposite points on the perimeter lie in the plane P1 that is oblique to the central axis CA1 of the tissue-removing element 20. The plane P1 may intersect a plane OP1 orthogonal to the central axis CA1 at an angle A1 measuring from about 5 degrees to about 45 degrees, or from about 10 degrees to about 30 degrees. For example, the plane P1 may intersect the orthogonal plane OP1 at an angle A1 of about 5 degrees, or 10 degrees, or 15 degrees, or 25 degrees, or 30 degrees, or 40 degrees, or 45 degrees. In one example, the angle A1 may measure about 10 degrees. In the illustrated embodiment, the proximal end portion of the tissue-removing element 20 is generally symmetrical about the central axis CA1. In particular, an entirety of the tissue-removing element 20 that is proximal of a proximal portion of the distal end face 100 is symmetrical circumferentially about the central axis CA1. In other words, other than the bevel of the distal end face 100, the tissue-removing element 20 may be generally symmetrical circumferentially about the central axis CA1.

In the embodiment illustrated in FIGS. 1-6, the distal end face 100 is generally planer and oblique (e.g., beveled), and lies in the plane P1 that is oblique to the central axis CA1 of the tissue-removing element 20. In the illustrated embodiment the distal end face 100 is free from abrasive material, although the distal end face may include abrasive material. The plane P1 in which the distal end face 100 lies may intersect a plane OP1 orthogonal to the central axis CA1 at an angle A1 measuring from about 5 degrees to about 45 degrees, or from about 10 degrees to about 30 degrees. For example, the plane P1 may intersect the orthogonal plane OP at an angle A of about 5 degrees, or 10 degrees, or 15 degrees, or 25 degrees, or 30 degrees, or 40 degrees, or 45 degrees. In one example, the angle A1 may measure about 10 degrees.

A distal opening 102 of the tissue-removing element 20 extends through the distal end face 100 such that the distal end face extends circumferentially about the distal opening. The central axis CA1 of the tissue-removing element 20 is coextensive with the axis of the distal opening 102 such that the distal end face 100 is oblique to the axis of the distal opening. In the illustrated embodiment, a distal end portion of the inner liner 14 and/or a distal end portion of the bearing 90 extends through the distal opening 102. The guidewire 26 is extendable through the distal opening 102 as it extends along the inner liner 14. The tissue-removing element 20 is configured to rotate concentrically about the guidewire when the guidewire is received in the inner liner 14. In another embodiment, one or both of the inner liner 14 and the bushing 90 may not extend through the distal opening 102. In yet another embodiment, one or both of the inner liner 14 and the bushing 90 may be omitted from the catheter 10, whereby the guidewire 26 may extend directly through the distal opening 102.

Figure 4:
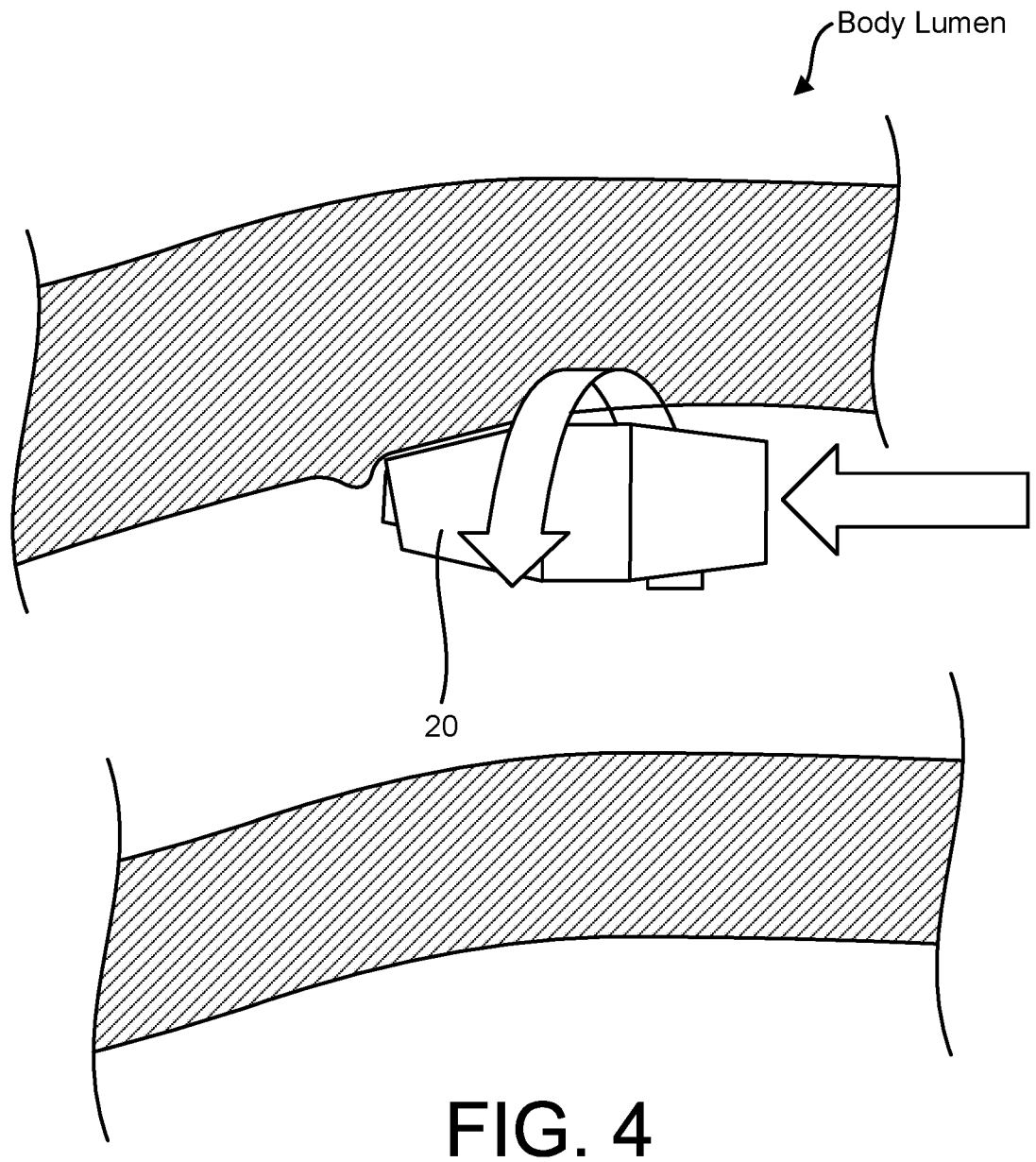
FIG. 4 is a schematic representation of a tissue-removing element of the tissue-removing catheter in engagement with an obstruction within a body lumen.
Figure 5:
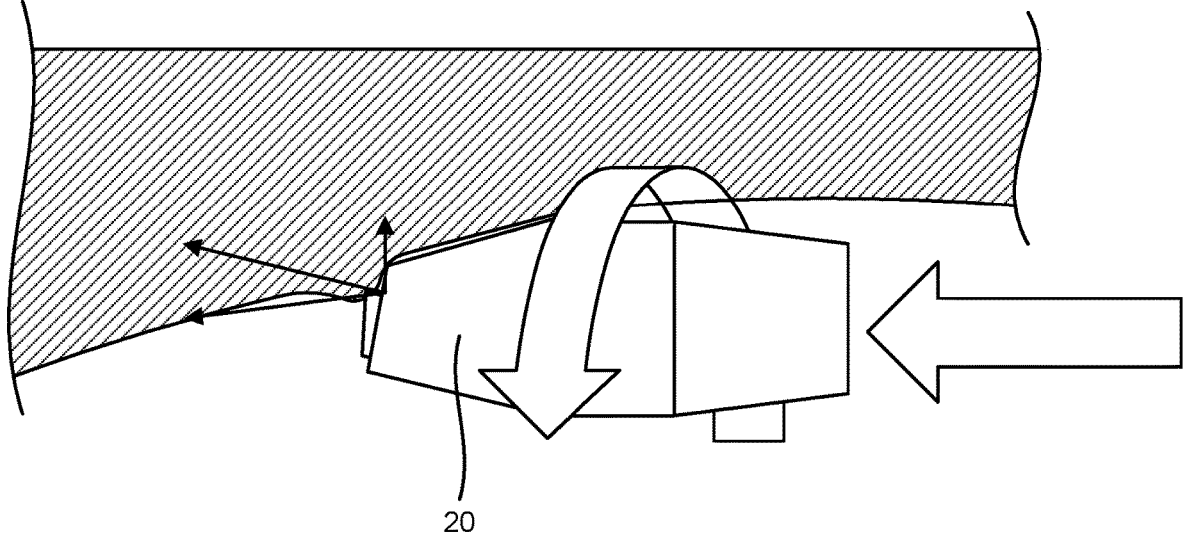
FIG. 5 is similar to FIG. 4, showing the tissue-removing element rotating around the obstruction.
Figure 6:
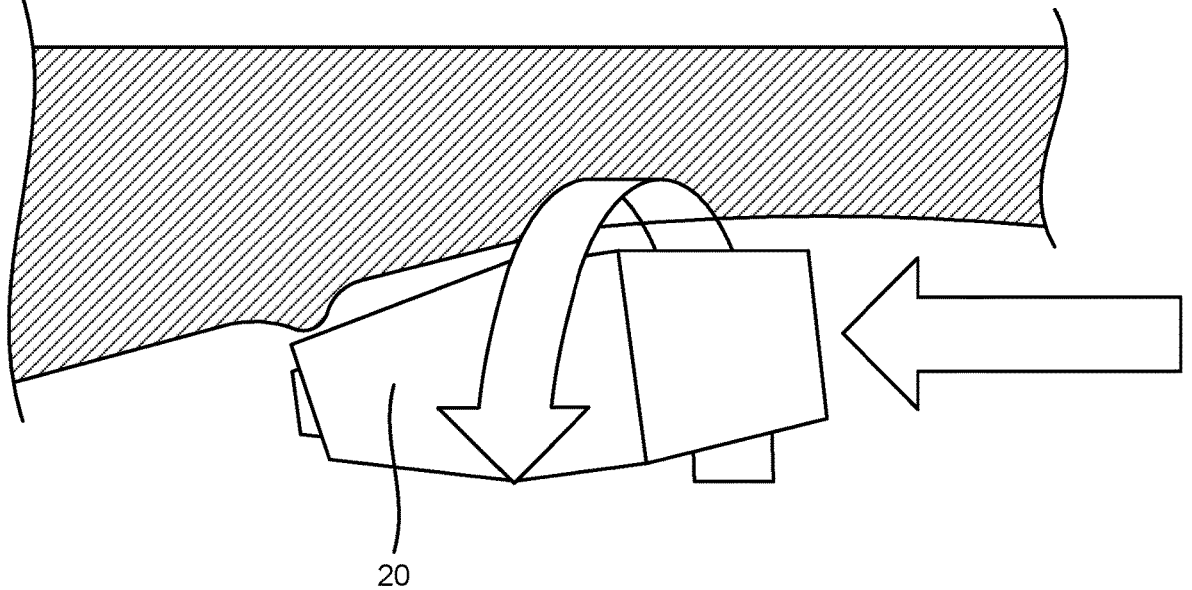
FIG. 6 is similar to FIG. 4, showing the tissue-removing element bypassing the obstruction.

Referring to FIGS. 4-6, in an exemplary method, the catheter body 12 is inserted into the body lumen (e.g., a blood vessel, such as an artery) to deliver the tissue-removing element 20 to the lesion or other tissue to be removed. As the tissue-removing element 20 is being delivered through the body lumen on a guidewire 26, for example, it may encounter an obstruction or "hang-up" on the wall of the body lumen, as shown in FIG. 4. It is desired to move the tissue-removing element 20 pass the obstruction in an efficient manner. The oblique distal end face 100 facilitates this bypassing movement. The tissue-removing element 20 can be rotated as it is tracked along the body lumen. The tissue-removing element 20 may be rotated continuously or in discrete increments as it is tracked along the body lumen. As the oblique distal end face 100 of the tissue-removing element 20 encounters the obstruction, the tissue-removing element 20 rotates away from the obstruction because of the rotating oblique distal end face which functions similar to a cam movement. As a result, as shown in FIG. 5, the instability of contact between the distal end face 100 and the obstruction reduces the potential hang ups. Thus, as shown in FIG. 6, the tissue-removing element 20 efficiently bypasses the obstruction. In addition, the oblique distal end face 100 may also improve the centering of the tissue-removing element 20 for ablation and lesion entry, along with potentially reducing the risk of the burr jumping forward on lesion breakthrough. The oblique distal end face 100 can also prevent the burr from burrowing into a "false lumen." Once the tissue-removing element 20 is delivered to the lesion, the tissue-removing element is rotated at a suitable ablation speed to debulk the lesion. When the practitioner is finished using the catheter, the catheter can be withdrawn from the body lumen and unloaded from the guidewire 26 by sliding the catheter proximally along the guidewire. The guidewire 26 used for the abrading process may remain in the body lumen for use in a subsequent procedure.

Figure 7:
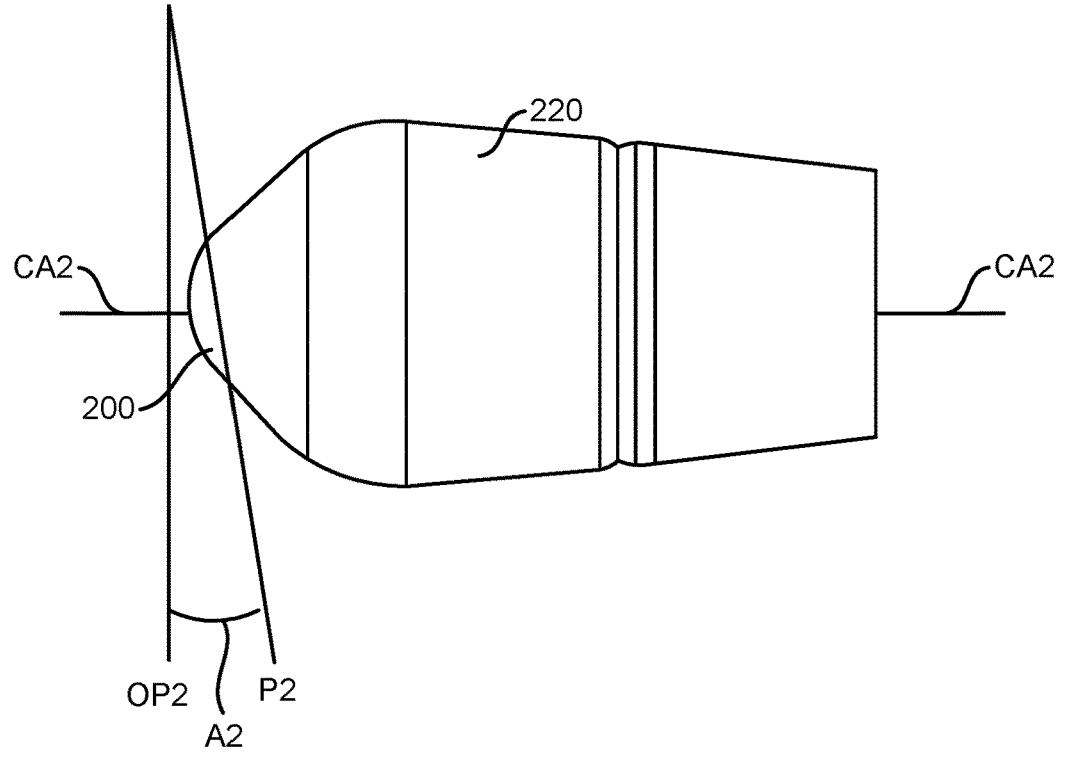
FIG. 7 is another embodiment of a tissue-removing element.

Referring to FIG. 7, a distal end face 200 of another tissue-removing element 220 is convex, such that the distal end face is not generally planar. However, like the first embodiment, the distal end face 200 has a perimeter and a diameter extending through the central axis CA2. At least some diametrically opposite points on the perimeter lie in a plane P2 that is oblique to the central axis CA2 of the tissue-removing element 220. In this and other embodiments, all diametrically opposite points on the perimeter lie in the plane P2 that is oblique to the central axis CA2 of the tissue-removing element 220. The plane P2 may intersect a plane OP2 orthogonal to the central axis CA2 at an angle A2 measuring from about 5 degrees to about 45 degrees, or from about 10 degrees to about 30 degrees. For example, the plane P2 may intersect the orthogonal plane OP2 at an angle A2 of about 5 degrees, or 10 degrees, or 15 degrees, or 25 degrees, or 30 degrees, or 40 degrees, or 45 degrees. In one example, the angle A2 may measure about 10 degrees. In the illustrated embodiment, the proximal end portion of the tissue-removing element 220 is generally symmetrical about the central axis CA2. In particular, an entirety of the tissue-removing element 220 that is proximal of a proximal portion of the distal end face 200 is symmetrical circumferentially about the central axis CA2. In other words, other than the bevel of the distal end face 200, the tissue-removing element

7

220 may be generally symmetrical circumferentially about the central axis CA2. The tissue-removing element 20 may be incorporated into the rotational tissue-removing catheter 10. The use and benefit of the tissue-removing element 220 may be similar to the first tissue-removing element 20.

Figure 8:
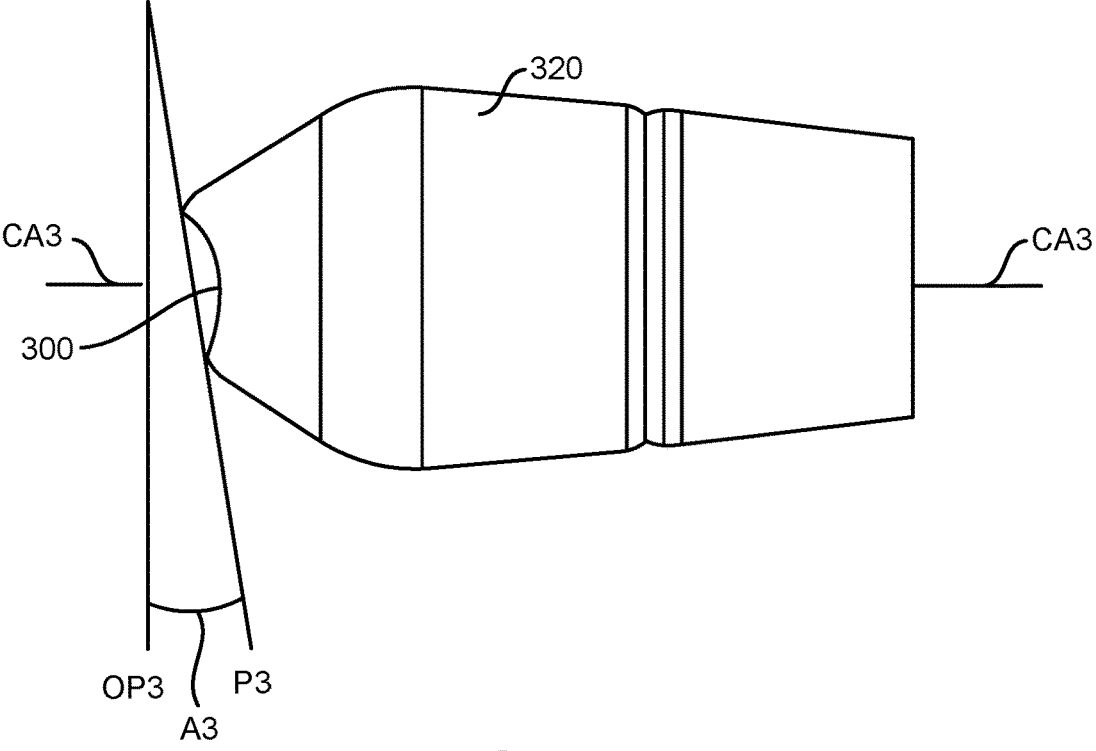
FIG. 8 is yet another embodiment of a tissue-removing element.

Referring to FIG. 8, a distal end face 300 of another tissue-removing element 320 is convex, such that the distal end face is not generally planar. However, like the first embodiment, the distal end face 300 has a perimeter and a diameter extending through the central axis CA3. At least some diametrically opposite points on the perimeter lie in a plane P3 that is oblique to the central axis CA3 of the tissue-removing element 320. In this and other embodiments, all diametrically opposite points on the perimeter lie in the plane P3 that is oblique to the central axis CA3 of the tissue-removing element. The plane P3 may intersect a plane OP3 orthogonal to the central axis CA3 at an angle A3 measuring from about 5 degrees to about 45 degrees, or from about 10 degrees to about 30 degrees. For example, the plane P3 may intersect the orthogonal plane OP3 at an angle A3 of about 5 degrees, or 10 degrees, or 15 degrees, or 25 degrees, or 30 degrees, or 40 degrees, or 45 degrees. In one example, the angle A3 may measure about 10 degrees. In the illustrated embodiment, the proximal end portion of the tissue-removing element 320 is generally symmetrical about the central axis CA3. In particular, an entirety of the tissue-removing element 320 that is proximal of a proximal portion of the distal end face 300 is symmetrical circumferentially about the central axis CA3. In other words, other than the bevel of the distal end face 300, the tissue-removing element 320 may be generally symmetrical circumferentially about the central axis CA3. The tissue-removing element 220 may be incorporated into the rotational tissue-removing catheter 10. The use and benefit of the tissue-removing element 320 may be similar to the first tissue-removing element 20.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A tissue-removing catheter for removing tissue in a body lumen, the tissue-removing catheter comprising:
a rotational drive shaft having a longitudinal axis and proximal and distal end portions spaced apart from one another along the longitudinal axis, the rotational drive shaft being sized and shaped to be received in the body lumen;
a drive operatively coupled to the proximal end portion of the rotational drive shaft and configured to impart rotation of the rotational drive shaft; and
a tissue-removing element operatively coupled to the distal end portion of the rotational drive shaft, the tissue-removing element having a central axis, proximal and a distal end portions spaced apart from one another along the central axis of the tissue-removing element, and an exterior surface,
wherein the tissue-removing element is configured to be rotated about its central axis via the rotational drive shaft to remove tissue from the body lumen,
wherein the distal end portion of the tissue-removing element defines an opening extending therethrough and includes a distal end face at a distal-most end of the tissue-removing element, the distal end face having an outer boundary at an intersection of the distal end face and the exterior surface, and an inner closed boundary at an intersection of the distal end face and an edge defining the opening, wherein the inner boundary is spaced inward from the outer boundary relative to the central axis,
wherein the outer and inner boundaries extend completely around the opening, such that the distal end face extends completely around the opening,
wherein an entirety of the distal end face is generally planar and lies generally within a plane that is oblique to the central axis of the tissue-removing element.

2. The tissue-removing catheter set forth in claim 1, further comprising an inner liner received in the tissue-removing element and configured to receive a guidewire therein.

3. The tissue-removing catheter set forth in claim 2, wherein the inner liner extends through the rotational drive shaft.

4. The tissue-removing catheter set forth in claim 2, wherein the inner liner extends through the elongate catheter body.

5. The tissue-removing catheter set forth in claim 2, further comprising a coupling assembly coupling the tissue-removing element to the inner liner.

6. The tissue-removing catheter set forth in claim 5, wherein the coupling assembly includes a bushing fixedly coupled to the inner liner, and at least one bearing ring coupled to the tissue-removing element and configured to rotate on an outer surface of the bushing as the tissue-removing element rotates about the central axis of the tissue-removing element.

7. The tissue-removing catheter set forth in claim 1, wherein the central axis of the tissue-removing element is coextensive with the longitudinal axis of the rotational drive shaft.

8. The tissue-removing catheter set forth in claim 1, wherein an outer surface of the tissue-removing element is abrasive and configured to abrade tissue from the body lumen.

9. The tissue-removing catheter set forth in claim 8, wherein the distal end portion of the tissue-removing element has an outer diameter that tapers distally to the distal end face.

10. A method of debulking a lesion in a blood vessel of a subject using the tissue-removing catheter set forth in claim 1, the method comprising:

advancing the tissue-removing element toward the lesion in the blood vessel; and rotating the tissue-removing element about its central axis simultaneously with said advancing the tissue-removing element, whereby rotation the tissue-removing element is configured to facilitate bypassing of the tissue-removing element if the distal end face engages an obstruction in the blood vessel as the tissue-removing element is advanced in the blood vessel.

11. The tissue-removing catheter set forth in claim 1, wherein the plane that is oblique to the central axis of the tissue-removing element intersects a plane orthogonal to the central axis at an angle measuring from about 5 degrees to about 45 degrees.

12. A tissue-removing catheter for removing tissue in a body lumen, the tissue-removing catheter comprising:

an elongate catheter body having a longitudinal axis and proximal and distal end portions spaced apart from one another along the longitudinal axis, the elongate catheter body being sized and shaped to be received in the body lumen;

a tissue-removing element operatively coupled to the distal end portion of the elongate catheter body, the tissue-removing element having a central axis and proximal and a distal end portions spaced apart from one another along the central axis of the tissue-removing element;

an inner liner received in the tissue-removing element and configured to receive a guidewire therein; and a bushing fixedly coupled to the inner liner, and at least one bearing ring coupled to the tissue-removing element and configured to rotate on an outer surface of the bushing as the tissue-removing element rotates about the central axis of the tissue-removing element, wherein the tissue-removing element is configured to be rotated to remove tissue from the body lumen, wherein the distal end portion of the tissue-removing element includes a distal end face at a distal-most end of the tissue-removing element, the distal end face extending completely around an opening, wherein the distal end face is generally planar and lies generally within a plane that is oblique to the central axis of the tissue-removing element, wherein a distal opening extends through the distal end face, wherein a distal end portion of the bushing extends distally outward from the distal opening of the distal end face of the tissue-removing element.

13. The tissue-removing catheter set forth in claim 12, wherein the distal end portion of the tissue-removing element has an outer diameter that tapers distally to the distal end face.

14. The tissue-removing catheter set forth in claim 12, wherein an outer surface of the tissue-removing element is abrasive and configured to abrade tissue from the body lumen.

15. The tissue-removing catheter set forth in claim 12, wherein a distal end portion of the inner liner extends distally outward from the distal opening of the distal end face of the tissue-removing element.

16. The tissue-removing catheter set forth in claim 15, wherein the distal end portion of the inner liner extends distally outward from the distal end face of the tissue-removing element.

* * * * *